US012650431B2

(12) United States Patent
Ka et al.

(10) Patent No.:  US 12,650,431 B2
(45) Date of Patent:  Jun. 9, 2026

(54) HUMAN IgG AUTOANTIBODIES AGAINST GALACTOSE-DEFICIENT IgA1, PREPARATION METHOD THEREOF, AND USE THEREOF

(71) Applicant: National Defense Medical Center, Taipei City (TW)

(72) Inventors: Shuk-Man Ka, Taipei City (TW); Chia-Chao Wu, Taipei City (TW); Ann Chen, Taipei City (TW)

(73) Assignee: National Defense Medical University, Taipei City (TW)

( * ) Notice: Subject to any disclaimer, the term of this patent is extended or adjusted under 35 U.S.C. 154(b) by 610 days.

(21) Appl. No.: 18/180,745

(22) Filed: Mar. 8, 2023

(65) Prior Publication Data

US 2023/0400468 A1      Dec. 14, 2023

(30) Foreign Application Priority Data

Jun. 8, 2022    (TW) ................................. 111121312

(51) Int. Cl.
G01N 33/577          (2006.01)

(52) U.S. Cl.
CPC ..... G01N 33/577 (2013.01); *G01N 2800/347* (2013.01)

(58) Field of Classification Search
CPC ........... G01N 33/577; G01N 2800/347; G01N 33/6854
See application file for complete search history.

(56) References Cited

U.S. PATENT DOCUMENTS

| | | | | |
|---|---|---|---|---|
| 2010/0015044 A1* | 1/2010 | Qiu | ........................ | A61K 49/14 424/1.49 |
| 2012/0114629 A1* | 5/2012 | Holyoak | ................. | A61P 17/00 435/219 |

FOREIGN PATENT DOCUMENTS

| | | | | |
|---|---|---|---|---|
| WO | WO-2010138621 A2 * | 12/2010 | ......... | G01N 33/6854 |
| WO | WO-2011038621 A1 * | 4/2011 | ............ | H04W 48/12 |
| WO | WO-2014004780 A1 * | 1/2014 | ....... | C07K 14/70521 |

* cited by examiner

*Primary Examiner* — Changhwa J Cheu

(74) *Attorney, Agent, or Firm* — MUNCY, GEISSLER, OLDS & LOWE, P.C.

(57) ABSTRACT

The current invention provides high specificity monoclonal antibodies, which can specifically bind to Gd-IgA as a novel non-invasive method for rapid diagnosing of IgAN subjects, which can be applied to unravel the mechanisms of IgA nephropathy and establish therapeutic strategies.

5 Claims, 13 Drawing Sheets

Specification includes a Sequence Listing.

| Target | 1 | | 2 | | 3 | | 4 | | 5 | | 6 | |
|---|---|---|---|---|---|---|---|---|---|---|---|---|
| Row\Column | KM55 | KC1 | KM55 | KC1 | KM55 | KC1 | KM55 | KC1 | KM55 | KC1 | KM55 | KC1 |
| A | HC1-F10E2 | | HC1-F10C6 | | HC1-F10B7 | | HC1-F10B4 | | HC1-F10D6 | | HC1-F10C7 | |
| | - | + | - | + | - | + | - | + | - | + | - | + |
| B | IgAN5-2E4E4 | | IgAN5-2E4B6 | | IgAN8-E8 | | IgAN9-E2 | | IgAN9-B6 | | IgAN9-E8 | |
| | - | + | + | + | + | + | - | + | - | + | - | + |
| C | IgAN7-1E4D2 | | IgAN7-1B8B2 | | IgAN10-E6 | | IgAN10-D10 | | IgAN10-1C6F3 | | IgAN10-2B5G7 | |
| | + | + | + | + | + | + | + | + | + | + | + | + |
| D | IgAN5-2E4D8 | | IgAN7-1E4E4 | | IgAN7-1E4D7 | | IgAN7-1E4E8 | | IgAN8-1E4D11 | | PBS | |

SEQUENCE LISTING

Sequence total quantity: 12
SEQ ID NO: 1              moltype = AA  length = 5
FEATURE                   Location/Qualifiers
source                    1..5
                          mol_type = protein
                          organism = unidentified
SEQUENCE: 1
DYAMH                                                                5

SEQ ID NO: 2              moltype = AA  length = 17
FEATURE                   Location/Qualifiers
source                    1..17
                          mol_type = protein
                          organism = unidentified
SEQUENCE: 2
GITWNSGTIG YADSVKG                                                  17

SEQ ID NO: 3              moltype = AA  length = 22
FEATURE                   Location/Qualifiers
source                    1..22
                          mol_type = protein
                          organism = unidentified
SEQUENCE: 3
YCAKVTTTYS STWYEAGAFD IW                                            22

SEQ ID NO: 4              moltype = AA  length = 10
FEATURE                   Location/Qualifiers
source                    1..10
                          mol_type = protein
                          organism = unidentified
SEQUENCE: 4
GFTFSNYAMT                                                          10

SEQ ID NO: 5              moltype = AA  length = 17
FEATURE                   Location/Qualifiers
source                    1..17
                          mol_type = protein
                          organism = unidentified
SEQUENCE: 5
SIRGGGAGAN YADSVKG                                                  17

SEQ ID NO: 6              moltype = AA  length = 17
FEATURE                   Location/Qualifiers
source                    1..17
                          mol_type = protein
                          organism = unidentified
SEQUENCE: 6
YCAKCSASLG NDAFDVW                                                  17

SEQ ID NO: 7              moltype = AA  length = 11
FEATURE                   Location/Qualifiers
source                    1..11
                          mol_type = protein
                          organism = unidentified
SEQUENCE: 7
RASQSISRWL A                                                        11

SEQ ID NO: 8              moltype = AA  length = 7
FEATURE                   Location/Qualifiers
source                    1..7
                          mol_type = protein
                          organism = unidentified
SEQUENCE: 8
KASTLES                                                              7

SEQ ID NO: 9              moltype = AA  length = 11
FEATURE                   Location/Qualifiers
source                    1..11
                          mol_type = protein
                          organism = unidentified
SEQUENCE: 9
CQHYNSYPWT F                                                        11

SEQ ID NO: 10             moltype = AA  length = 17
FEATURE                   Location/Qualifiers
source                    1..17
                          mol_type = protein
                          organism = unidentified -continued

```
SEQUENCE: 10
KSSQSILHSS NSRDYLA                                                    17

SEQ ID NO: 11          moltype = AA  length = 7
FEATURE                Location/Qualifiers
source                 1..7
                       mol_type = protein
                       organism = unidentified
SEQUENCE: 11
WASARES                                                                7

SEQ ID NO: 12          moltype = AA  length = 10
FEATURE                Location/Qualifiers
source                 1..10
                       mol_type = protein
                       organism = unidentified
SEQUENCE: 12
CQQYYDAWTF                                                            10
```

| | - | - | - | - | - | - | - | - | - | - | - | - |

HUMAN IgG AUTOANTIBODIES AGAINST GALACTOSE-DEFICIENT IgA1, PREPARATION METHOD THEREOF, AND USE THEREOF

REFERENCE TO AN ELECTRONIC SEQUENCE LISTING

The application contains a Sequence Listing which has been submitted electronically in .XML format and is hereby incorporated by reference in its entirety. Said. XML copy, created on Dec. 24, 2025, is named "2026 Jan. 7-Sequence-Listing.xml" and is 26,000 bytes in size. The sequence listing contained in this XML file is part of the specification and is hereby incorporated by reference herein in its entirety.

CROSS-REFERENCE TO RELATED APPLICATIONS

This Non-provisional application claims priority under 35 U.S.C. § 119(a) on Patent Application No(s). 111121312 filed in Taiwan, Republic of China on Jun. 8, 2022, the entire contents of which are hereby incorporated by reference.

FIELD OF THE INVENTION

The present invention relates to a liquid kidney biopsy reagent set including antibodies that can be used for non-invasive and early diagnosis of IgA glycosyl abnormalities.

BACKGROUND OF THE INVENTION

IgA nephropathy (IgAN) is the most common primary glomerulonephritis in the world. Studies have shown that IgA nephropathy is related to the abnormality of O-glycosyl deficient galactose IgA1 (Gd-IgA1), IgA and the complement system forms an immune complex, which precipitates in the glomerulus to activate immune cells and produce cytokines and chemokines. Chemokine stimulates the inflammatory response, promotes renal cell proliferation, and damages podocytes and renal tubules. Today, there is no precise medical strategy for IgA nephropathy, so when patients have symptoms of uremia, they can only receive dialysis treatment or kidney transplantation.

Currently, IgA nephropathy can only be diagnosed through invasive kidney biopsy sections and the use of immunofluorescence microscopy to examine kidney tissue at clinical, it will affect the target of early diagnosis and early treatment, and in addition to the pathogenesis of IgA nephropathy is still unclear, and it is impossible to explain exactly the immune complex is form by which of galactose-deficient IgA1 and which anti-galactose-deficient IgA1 IgG. On the other hand, in this precise treatment era, it is an urgent and important issue to develop a non-invasive IgA nephropathy diagnostic method and analytical reagent kits for effective diagnosis and to provide the best follow-up treatment strategy.

SUMMARY OF THE INVENTION

For this reason, an object of the present invention is to develop a liquid kidney biopsy detecting reagent kits use for non-invasive, early stage, rapid diagnosis, and specificity of IgA glycosyl abnormalities.

Another aspect of the present invention provides a method for detecting an abnormality in an individual IgA glycosylation, the method comprising utilizing a detection reagent including at least one monoclonal antibody in the individual.

BRIEF DESCRIPTION OF THE DRAWINGS

FIG. 1A-1D show the analysis of the expression of the monoclonal antibody galactose-deficient IgA1 confirmed by KM55/KCl dot blot. Among them, the supernatant of poly-clonal IgA-secreting hybridoma cells was loaded on a nitro-cellulose membrane, followed by Rabbit anti-Human IgA1 (FIG. 1A); KM55 (FIG. 1B) and KCl dot blot method (FIG. 1C) identification of galactose-deficient IgA1. HC in the diagram represents Health control; IgAN represents IgA nephropathy. FIG. 1D is the result of the example.

FIG. 3A and FIG. 3B are the ELISA binding test analysis to confirm that the monoclonal secreted anti-galactose-deficient IgA1 IgG autoantibody and untreated IgA1 (Intact-IgA1) and self-prepared Gd-IgA1. I-IgA1 Intact-IgA1; Gd-IgA1, Galactose-deficient IgA1.

FIG. 4A and FIG. 4B are the ELISA analysis in different galactose-deficient gly-copeptides to detect the specific binding sites of 16-3D5E3 and 18-2E9D2. FIG. 4C and FIG. 4D show the ELISA analysis of IgG subsets detected in 16-3D5E3 and 18-2E9D2.

FIG. 5A and FIG. 5B are the binding test of IgG16-3D5E3 (SEQ ID NO: 3) and 18-2E9D2 (SEQ ID NO: 6) IgG autoantibody to galactose-deficient IgA1 and normal IgA1. FIG. 5C and FIG. 5D are the verification of galactose-deficient IgA1 and normal IgA1 by using KCl ELISA and KM55 ELISA.

DETAILED DESCRIPTION OF THE INVENTION

Figure 1A:
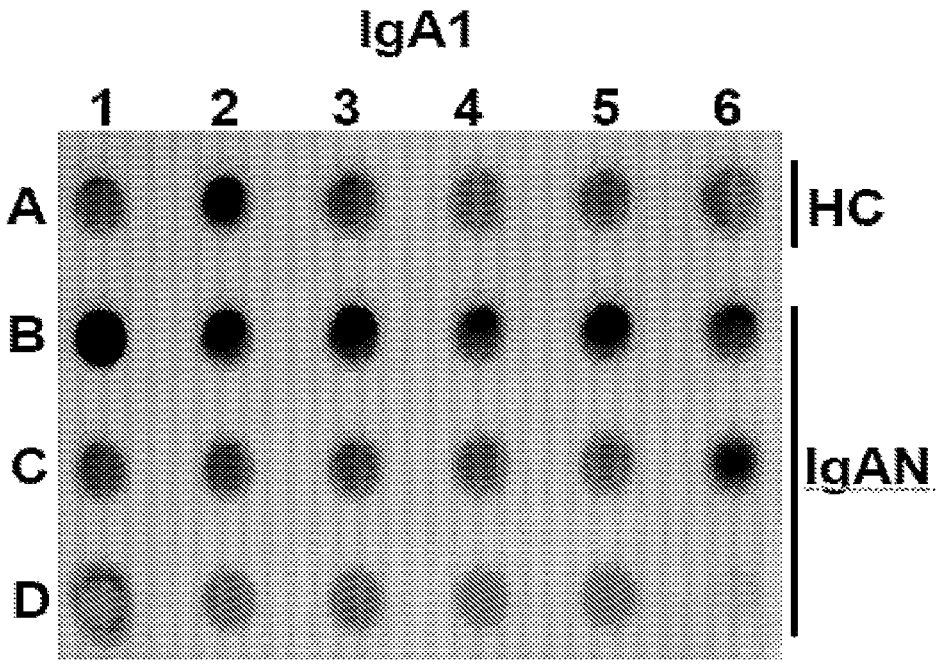

The following definitions are intended to clarify, but not limit in the defined terms. A particular term used herein should not be considered ambiguous if it is not specifically defined. Those terms are used within their acceptable meanings by those skilled in the art. In one embodiment, the monoclonal antibodies of the present invention are include, but are not limited to SEQ ID NO: 1 to SEQ ID NO: 12.

TABLE 1

| The sequence of monoclonal antibody | | |
| --- | --- | --- |
| Name | sequence | Description |
| SEQ ID NO: 1 | DYAMH | the first antibody Ig heavy chain of CDR1 |
| SEQ ID NO: 2 | GITWNSGTI GYADSVKG | the first antibody Ig heavy chain of CDR2 |

TABLE 1-continued

The sequence of monoclonal antibody

| Name | sequence | Description |
|---|---|---|
| SEQ ID NO: 3 | YCAKVTTTY SSTWYEAGA FDIW | the first antibody Ig heavy chain of CDR3 |
| SEQ ID NO: 4 | GFTFSNYAM T | the second antibody Ig heavy chain of CDR1 |
| SEQ ID NO: 5 | SIRGGGAGA NYADSVKG | the second antibody Ig heavy chain of CDR2 |
| SEQ ID NO: 6 | YCAKCSASLG NDAFDVW | the second antibody Ig heavy chain of CDR3 |
| SEQ ID NO: 7 | RASQSISRW LA | the first antibody Ig light chain of CDR1 |
| SEQ ID NO: 8 | KASTLES | the first antibody Ig light chain of CDR2 |
| SEQ ID NO: 9 | CQHYNSYPW TF | the first antibody Ig light chain of CDR3 |
| SEQ ID NO: 10 | KSSQSILHSS NSRDYLA | the second antibody Ig light chain of CDR1 |
| SEQ ID NO: 11 | WASARES | the second antibody Ig light chain of CDR2 |
| SEQ ID NO: 12 | CQQYYDAWTF | the second antibody Ig light chain of CDR3 |

In one embodiment of the present invention, the IgG autoantibody was screened by the hybridoma cells secreted. Dilute IgA1 (I-IgA1) (Immunoreagent; USA) and galactose-deficient IgA1 (Gd-IgA1) by home-made in PBS at 0.2 μg per well, and add 50 μl at 4° C. until the next day. Then, using 200 μl Wash Buffer (0.05% PBST) to wash the 96-well plate, removing the liquid, and adding 200 μl Blocking Buffer (1% BSA/PBST) for 1 hour at room temperature. Adding 50 μl of hybridoma cell supernatant or purified IgG to the 96-well plate and affect at 37° C. for 2 hours after washing. Then after washing, adding 50 μl of Goat anti IgG 10000-fold diluted in Blocking Buffer and blocking for 1 hour at 37° C. After washing, using Donkey anti goat-HRP 10000 times to dilute in Blocking Buffer, then adding 50 μl to 96-well plate and keep it in the dark at 37° C. for 1 hour. After washing, adding TMB color reagent to react for 15 minutes, and finally adding 50 μl stop solution (2N $H_2SO_4$) to stop the reaction, and using an ELISA reader to detect the absorbance at OD 450 nm. Dilute IgG autoantibody at 20 μg/ml per well in PBS, add 50 μl, and react at 4° C. until the next day, wash the 96-well plate with 200 μl Wash Buffer (0.05% PBST), remove the liquid, and add 300 μl Blocking Buffer (1% BSA/PBST) blocking for 1 hour at 37° C., after washing, adding 100 μl, 0.5 μg/well of galactose-deficient glycopeptides at different sites and bind to HCR (T225, VPST(GalNAc)PPTPSPSTPPTPSPSC-NH2 (SEQ ID NO: 13); T228, VPSTPPT(GalNAc)PSPSTPPTPSPSC-NH2 (SEQ ID NO: 14); S230, VPSTPPTPS(GalNAc) PSTPPTPSPSC-NH2 (SEQ ID NO: 15); S232, VPSTPPTPSPS(GalNAc)TPPTPSPSC-NH2 (SEQ ID NO:

16); S233, VPSTPPTPSPST(GalNAc)PPTPSPSC-NH2 (SEQ ID NO: 17); T236, VPSTPPTPSPSTPPT(GalNAc) PSPSC-NH2 (SEQ ID NO: 18); All-HR, VPST(GalNAc) PPT(GalNAc)PS(GalNAc)PS(GalNAc)T (GalNAc)PPT (GalNAc)PSPSC-NH2 (SEQ ID NO: 19); HR, VPSTPPTPSPSTPPTPSPSC-NH2 (SEQ ID NO: 20)) to a 96-well plate for 2 hours at 37° C., after washing, add 100 μl HRP conjugated Rabbit anti-6-His Tag (ICAlab) was diluted 10,000 times in Blocking Buffer and affect at 37° C. for 1 hour. After washing, 100 μl of TMB color reagent was added to react for 15 minutes. Finally, added 50 μl of stop solution (2N $H_2SO_4$) to stop the reaction, and ELISA was used. The reader detects absorbance at OD 450 nm.

EXAMPLES

Other specific embodiments of the present invention are including, but are not limited to the following embodiments.

Example 1

Establishment and Verification of the Secretion of Human Galactose-Deficient IgA1 and IgG Autoantibody Monoclonal Hybridoma With the approval of the Institutional Review Board (IRB) in several hospitals, we obtained peripheral blood mononuclear cells (PBMC) and human megakaryocyte leukemia cell lines from 15 IgAN patients, and culture with the fusion partner cell, which were fusion of human megakaryoblastic leukemia cell line (MEG-01) and SP2 mouse myeloma cells, to get then hybridomas were acquired.

Then using IgA/IgG (Total) Human Uncoated ELISA Kit (ThermoFisher) to conduct the first screening of immunoglobulin typing. It was detected whether the hybridoma cells can produce immunoglobulin IgA, and furthermore screen that whether has the galactose defect in IgA. In addition, it was also detected whether the hybridoma cells can be produced immunoglobulin IgG and furthermore screen that whether the IgG could identify the galactose-deficient IgA1.

Example 2

The Galactose-Deficient IgA1 Screening of IgA Positive Hybridoma

IgA-positive hybridomas were screened by dot blot. The supernatant of the aforementioned hybridoma cells was loaded onto a 0.45 μm pore size Nitrocellulose membrane, and the millipore filtration system (Bio-Dot®) Microfiltration System, Bio-Rad Laboratories, Inc.) to use for screening experiments. At the same time, Anti-human Gd-IgA1 (KM55) Rat IgG, which is known to bind to galactose-deficient IgA1, and KCl lectin, which has a good specific affinity for GalNAc carbohydrates, were also used in the experiments. Analysing percentage of detection rate of galactose-deficient IgA1 in 15 patients, and processing to limiting dilution multiple hybridomas to find out single clone of hybridoma.

Example 3

Figure 1B:
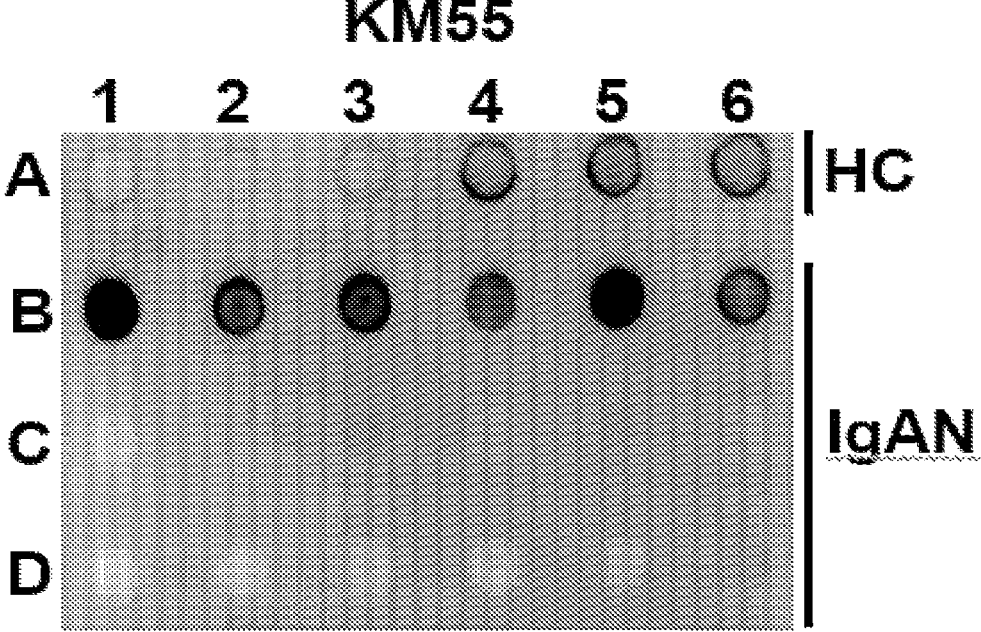
Figure 1C:
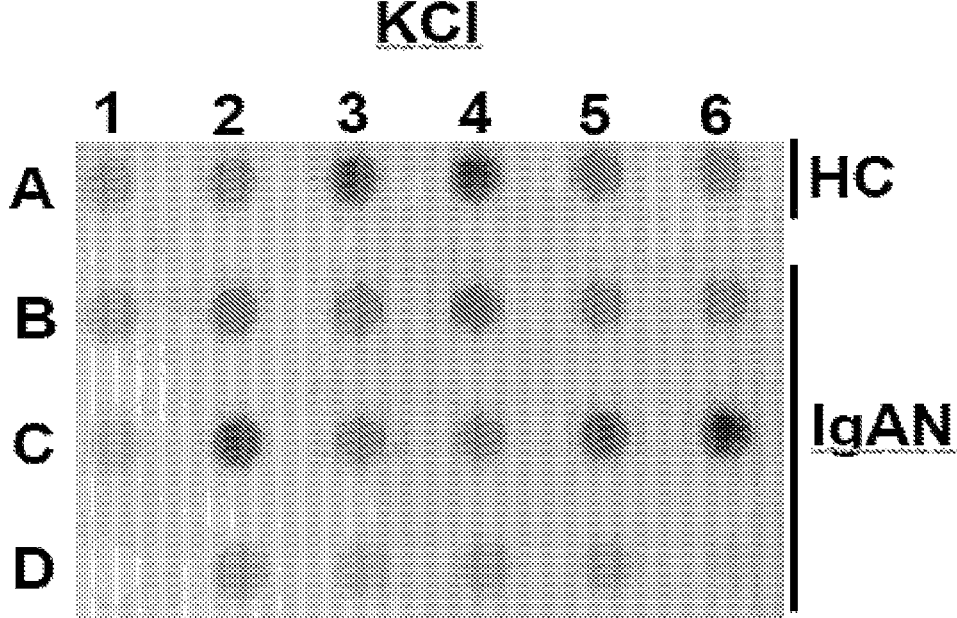

The Acquisition of the IgA1 Cell Strain of Individual Human Galactose Deficiency Amplifying the multi-strain hybridomas of the IgA1 screened for galactose deficiency, and subsequently obtaining monoclonal antibodies by limiting dilution. The screening method is the same as the aforementioned KM55/KCl dot blot experiment. The results show that the human galactose-deficient IgA1 antigen secreted by different single clone of hybridoma cell lines has different degrees of defect and different glycosylation sites. For example, one of the monoclonal antibodies, IgAN5-2E4E4, can be strongly recognized by KM55 (FIG. 1B). In KCl, IgAN10-2B5G7 is the most recognized, and the remaining monoclonal antibodies are weaker than IgAN10-2B5G7 (FIG. 1C). This result indicates that the antigenic galactose-deficient IgA1 is different in each patient.

Example 4

Confirming the IgA1 of Galactose Defect by Western Blot

Figures 2A, 2B, 2C:
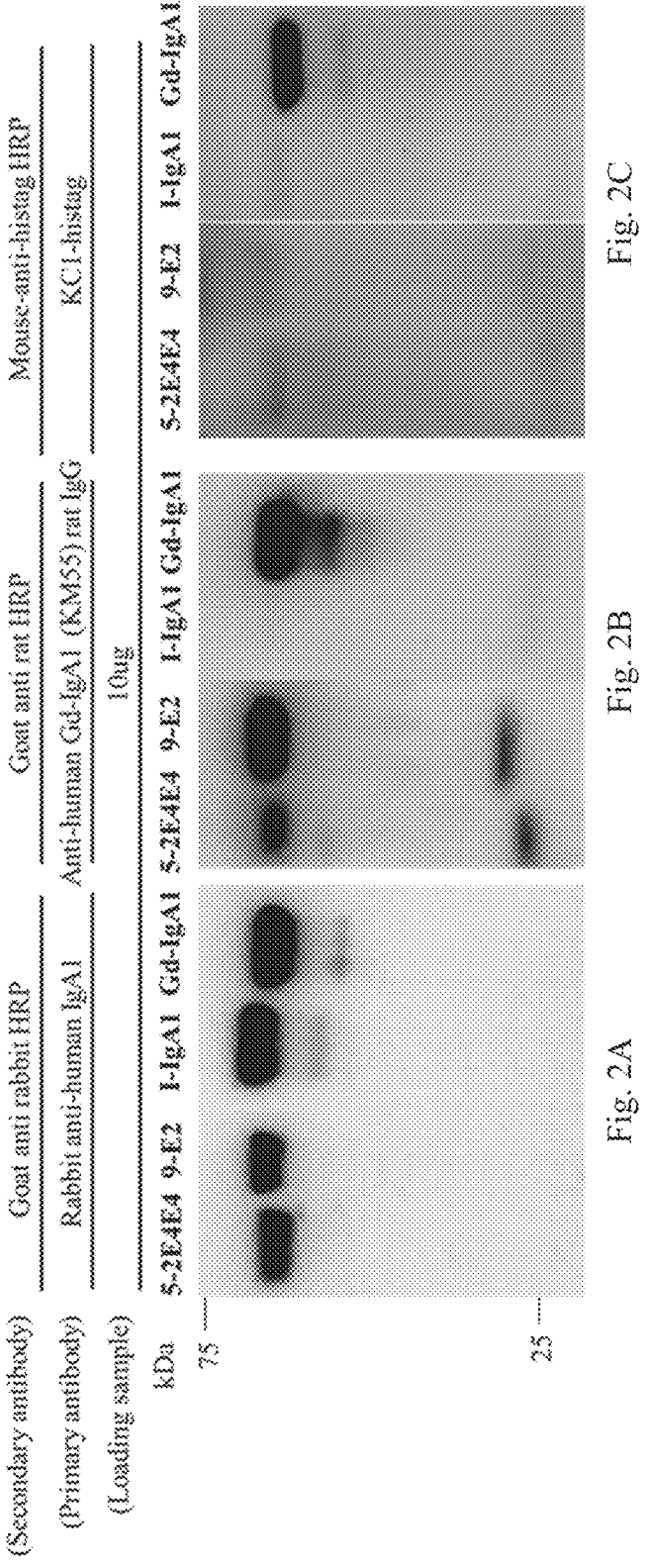
FIG. 2A-2C illustrates the test of the present invention to confirm the galactose-deficient IgA1 cell line by the western blot. Using jacalin-Sepharose Beads column purified the galactose-deficient IgA1 cell lines 5-2E4E4 and 9-E2, and then analyzed the galactose-deficient IgA1 by Western blot. Using (1) Rabbit anti-Human IgA1 (FIG. 2A); (2) Anti-human Gd-IgA1 (KM55) Rat IgG (FIG. 2B) and KCl combined with 5-2E4E4 and 9-E2 purified proteins (FIG. 2C). I-IgA1 and homemade galactose-deficient IgA1 were used as controls. I-IgA1, Intact-IgA1; Gd-IgA1, Galactose-deficient IgA1.

Collecting the supernatant from monoclonal hybridoma cell lines that can secrete galactose-deficient IgA1, and using the jacalin-Sepharose Beads column to purify the galactose-deficient IgA1. Furthermore, the performance of galactose-deficient IgA1 was analyzed by Western blot. The results showed that IgA1 (FIG. 2A), KM55 (FIG. 2B), and KCl (FIG. 2C) could be recognized by IgAN5-2E4E and 9-E2. In comparison to the self-prepared standard samples of I-IgA1 and Gd-IgA1, it was found that the heavy chain molecular weight in IgAN5-2E4E was significantly reduced due to the absence of sugar residues, which indicates that the individual variability of galactose-deficient IgA1 glycosylation abnormalities among patients is evident.

Example 5

Figure 3A:
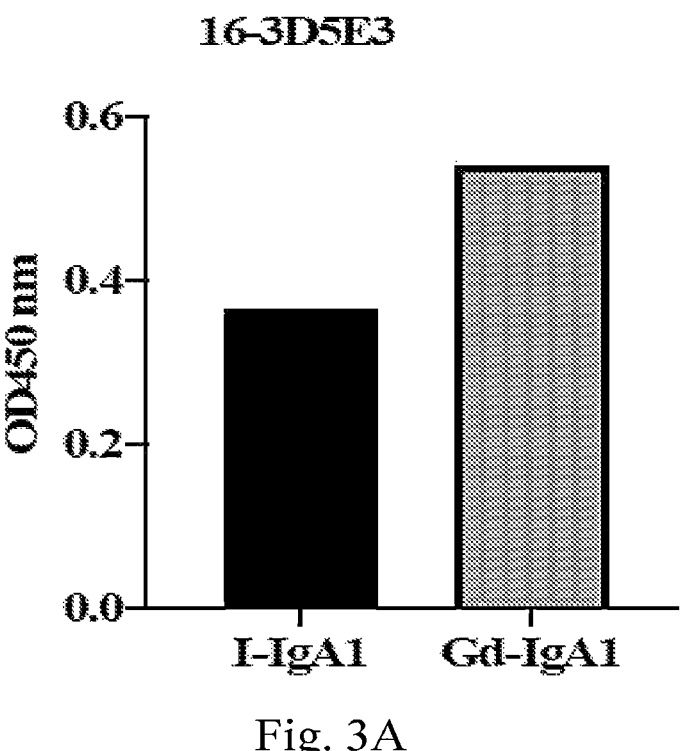
FIG. 3A-3B shows the binding test of IgG autoantibody to IgA1.
Figure 3B:
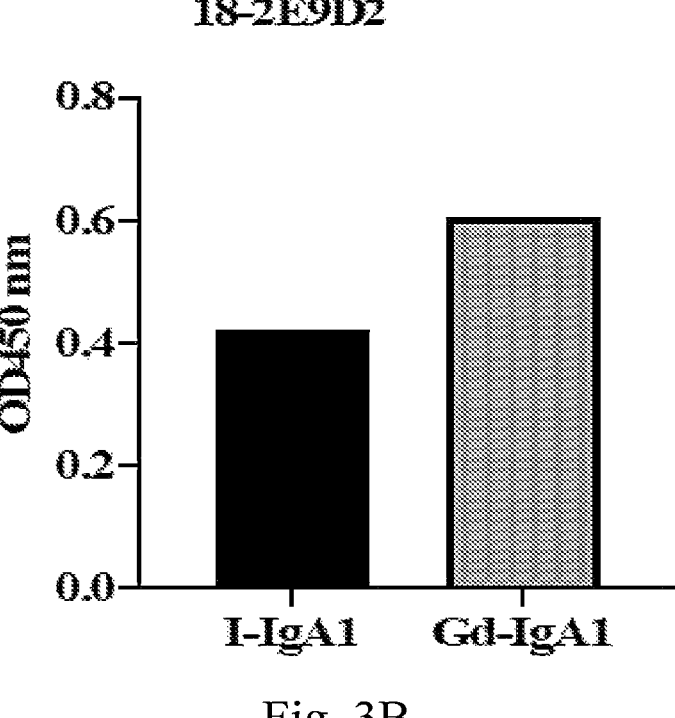

Screening of Hybridomas Producing IgG-Positive Antibodies Against Abnormally Glycosylated IgA1 Autoantibodies After the IgG typing was confirmed, the preparation of desialylated immunoglobulin A1 (Sd-IgA1) was used by neuraminidase. Then, galactose-deficient immunoglobulin A1 (Gd-IgA1) and intact IgA1 were prepared using β-galactosidase. ELISA was used for screening. For example, the No. IgAN18 showed in the 23 wells of the 96-well plate was IgG antibodies. Polyclonal hybridoma No. 18-2E9D2 could recognize Galactose-deficient IgA1 (Gd-IgA1) better than intact IgA1 (I-IgA1). On the other side, polyclonal hybridoma No. 16-3D5E3 could recognize intact IgA1 (I-IgA1) better than Galactose-deficient IgA1 (Gd-IgA1) (FIGS. 3A and 3B).

Therefore, it is considered that one antibody recognizing IgA1 was as an IgG in the primary screening. The detection rate of IgG autoantibody in 15 patients was analyzed, then monoclonal antibodies were performed by subsequently limited dilution.

Thus, monoclonal antibodies were performed by 16-3D5E3 and 18-2E9D2 via subsequently diluted. Monoclonal antibodies 16-3D5E3 (SEQ ID NO: 3) and 18-2E9D2 (SEQ ID NO: 6), as well as other patients monoclonal autoantibodies were recognized I-IgA1 and Gd-IgA to be screened by ELISA again. Cell supernatant was purified by Protein G. The autoantibody IgG protein was quantified and binding ELISA was performed with I-IgA1 and Gd-IgA1. The results showed that SEQ ID NO: 3 and SEQ ID NO: 6 recognized Gd-IgA1 better than I-IgA1.

Example 6

The Binding Site of Monoclonal Autoantibody

Figure 4A:
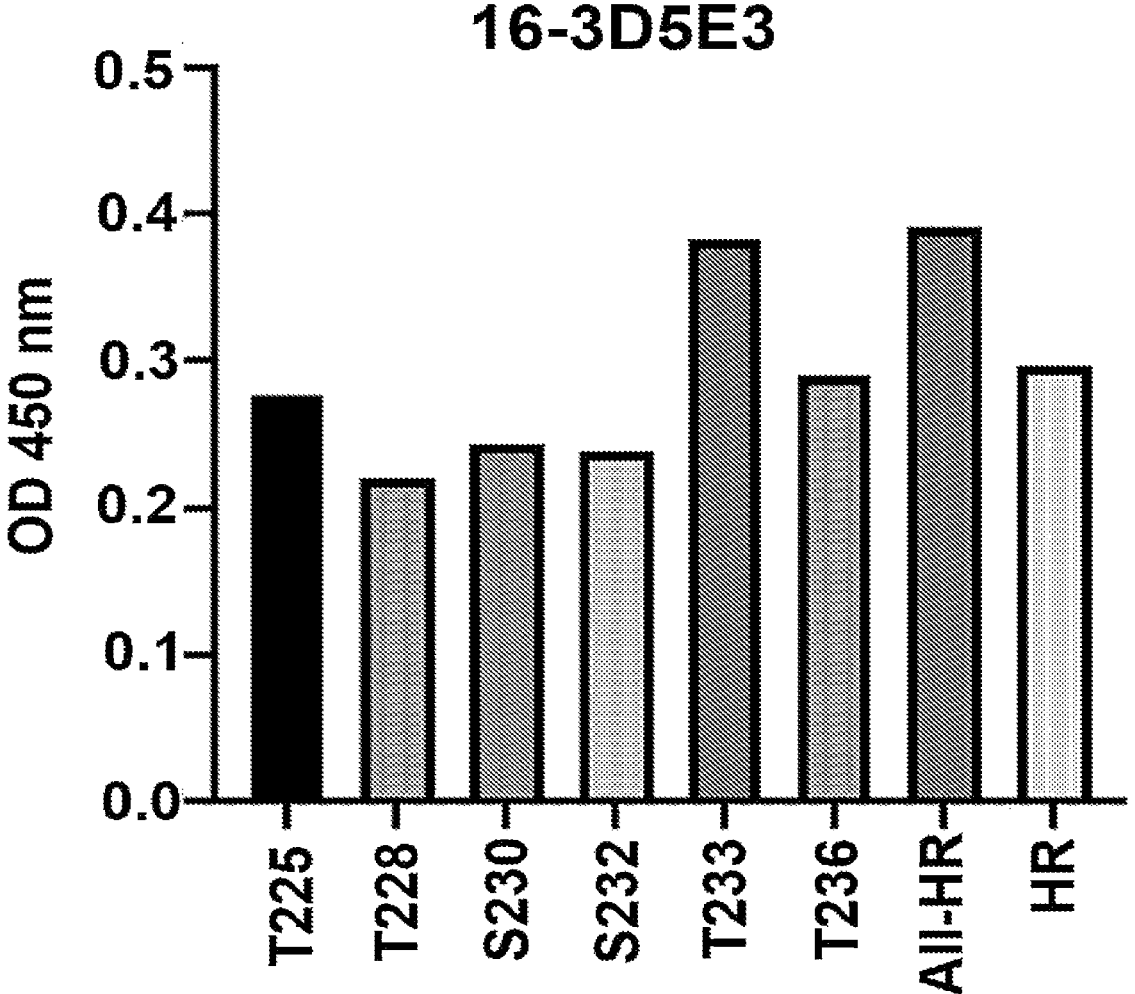
FIG. 4A-4D shows the analysis and comparison of the characteristics of IgG autoantibody.
Figure 4B:
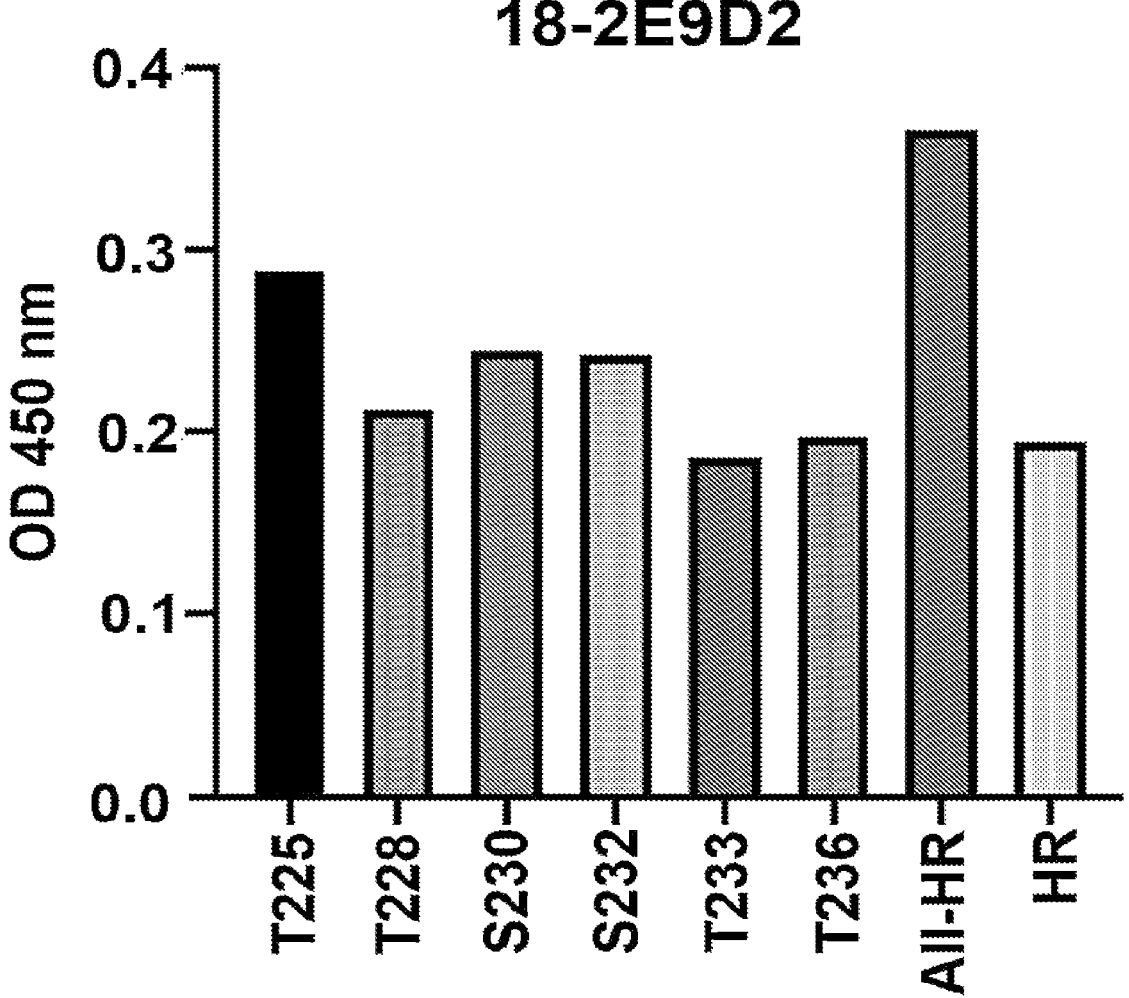

After the autoantibody has the properties that can be confirmed to recognize IgA1, further analysing its binding site (Epitope). Glycosylation of the hinge region sequence on the mimic galactose-deficient IgA1 to synthesize glycopeptides at different sites and attach to HCRC with Histag to detect the specific recognition binding site of the antibody and the epitope of the antibody. The results showed that the 16-3D5E3 (SEQ ID NO: 3) IgG autoantibody had the greatest binding to T233 and All-HR (FIG. 4A), while 18-2E9D2 (SEQ ID NO: 6) IgG autoantibody binds the most to T225, S230, S232 and All-HR (FIG. 4B). The results showed that the IgG autoantibody produced in each patient was different in identifying galactose-deficient IgA1.

Example 7

The Analysis of the IgG Subgroup of Monoclonal Autoantibody

Figure 4C:
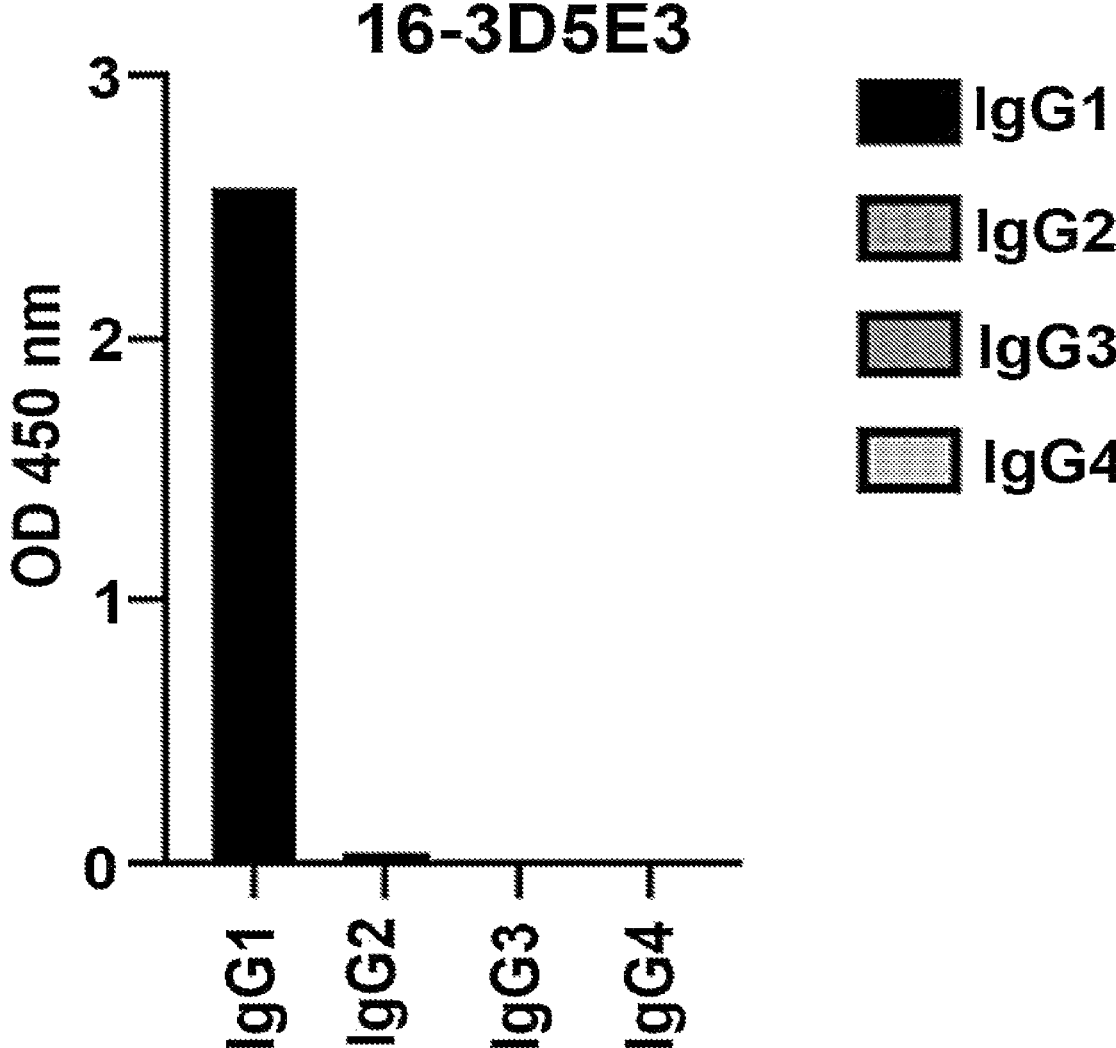
Figure 4D:
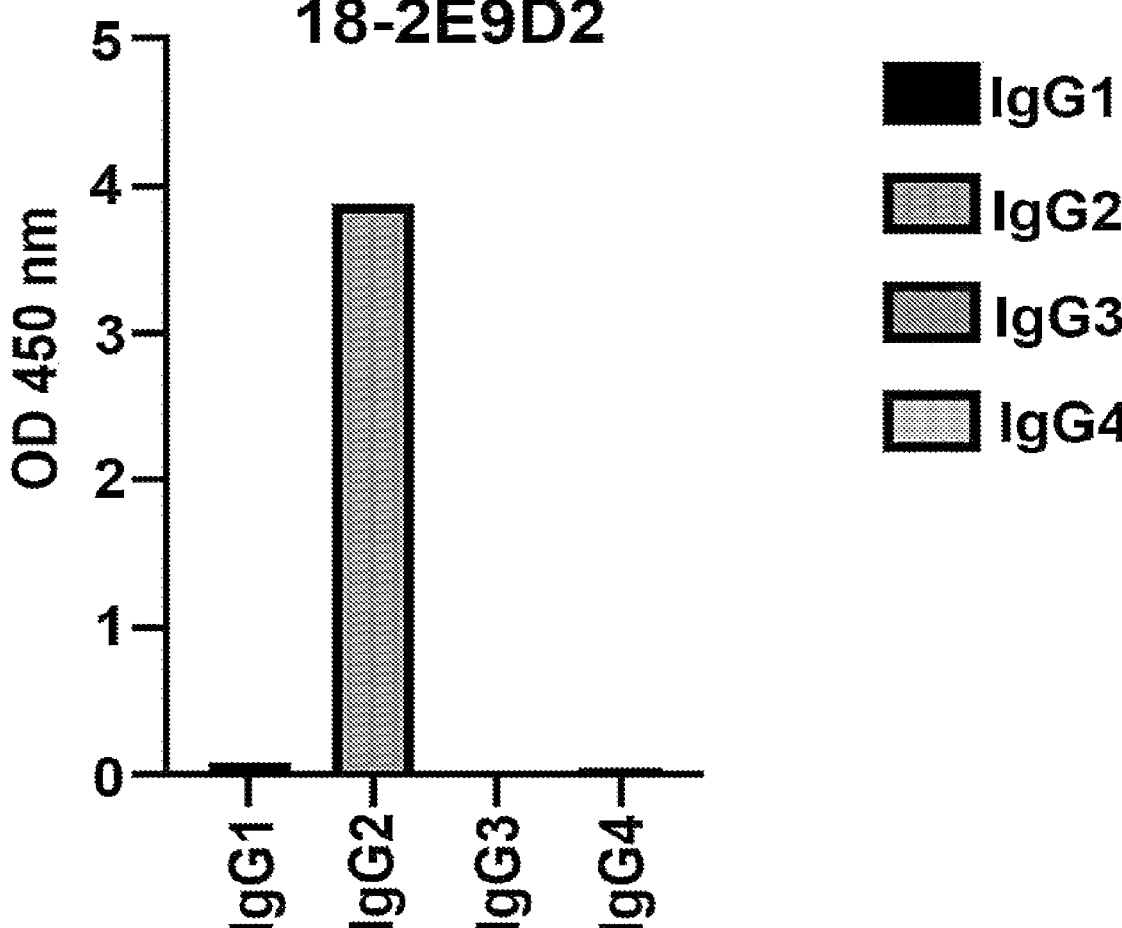

The two strains of autoantibodies were analyzed by IgG Subclass Human ELISA Kit (TheromFisher), and the results showed that 16-3DE3 (SEQ ID NO: 3) was IgG1, and 18-2E9D2 (SEQ ID NO: 6) was IgG2 (FIG. 4C).

Example 8

The IgG Sequence Analysis of Monoclonal Autoantibody

The 16-3D5E3 (SEQ ID NO: 3) and 18-2E9D2 (SEQ ID NO: 6) monoclonal hybridoma cells were sequenced, and the results showed that 16-3D5E3 (SEQ ID NO: 3) was YCAKVTTTYSSTWYEAGAFDIW and 18-2E9D2 (SEQ ID NO: 6) is YCAKCSASLGNDAFDVW. 16-3D5E3 (SEQ ID NO: 3) and 18-2E9D2 (SEQ ID NO: 6) are Kappa light chains.

Example 9

The Binding Test of Autoimmune Complex

Figure 5A:
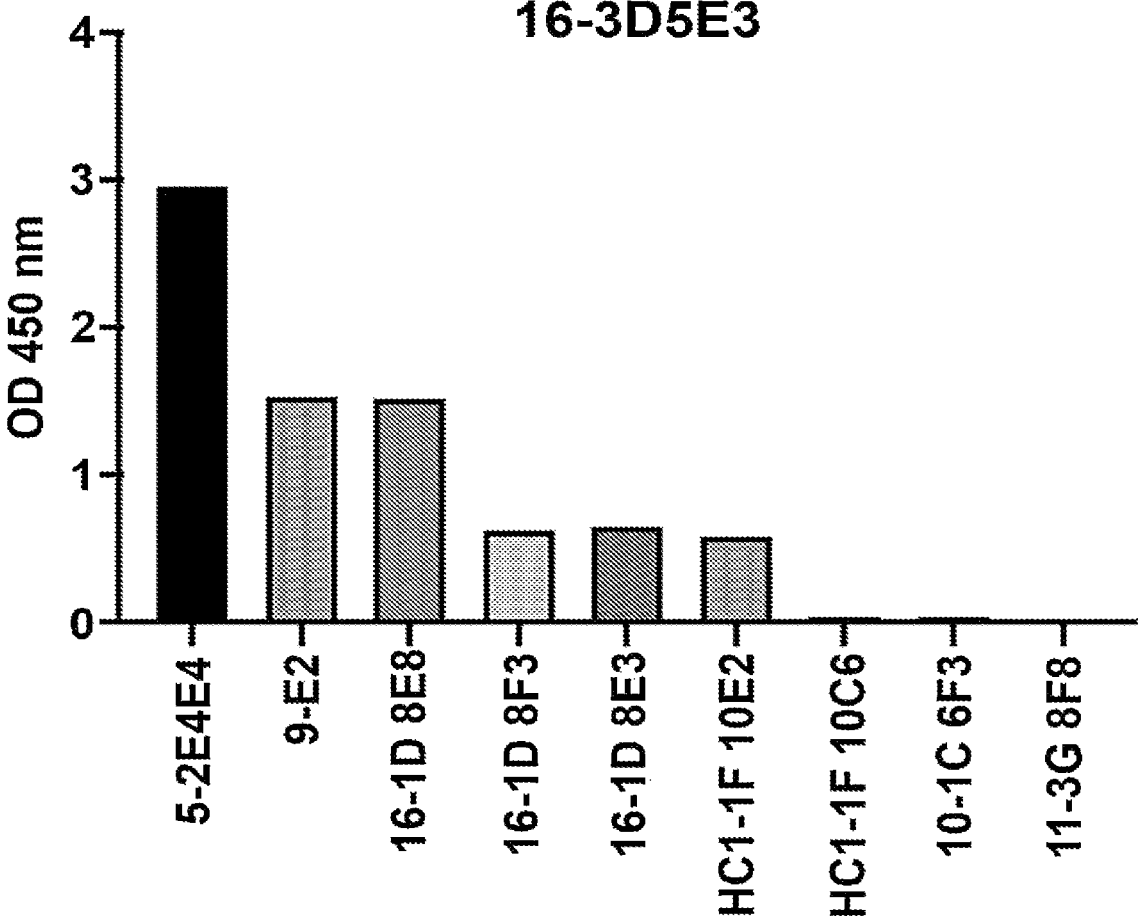
FIG. 5A-5D shows the binding assay of autoimmune complexes.
Figure 5B:
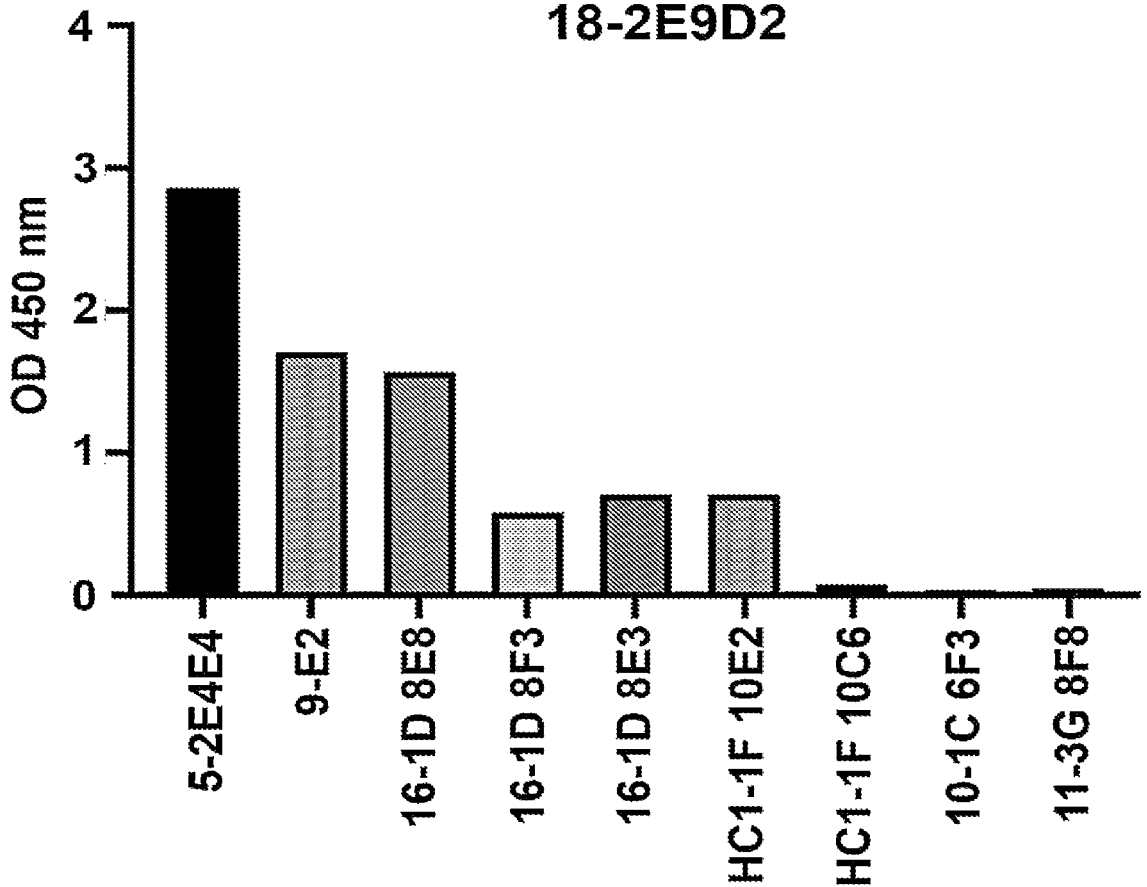
Figure 5C:
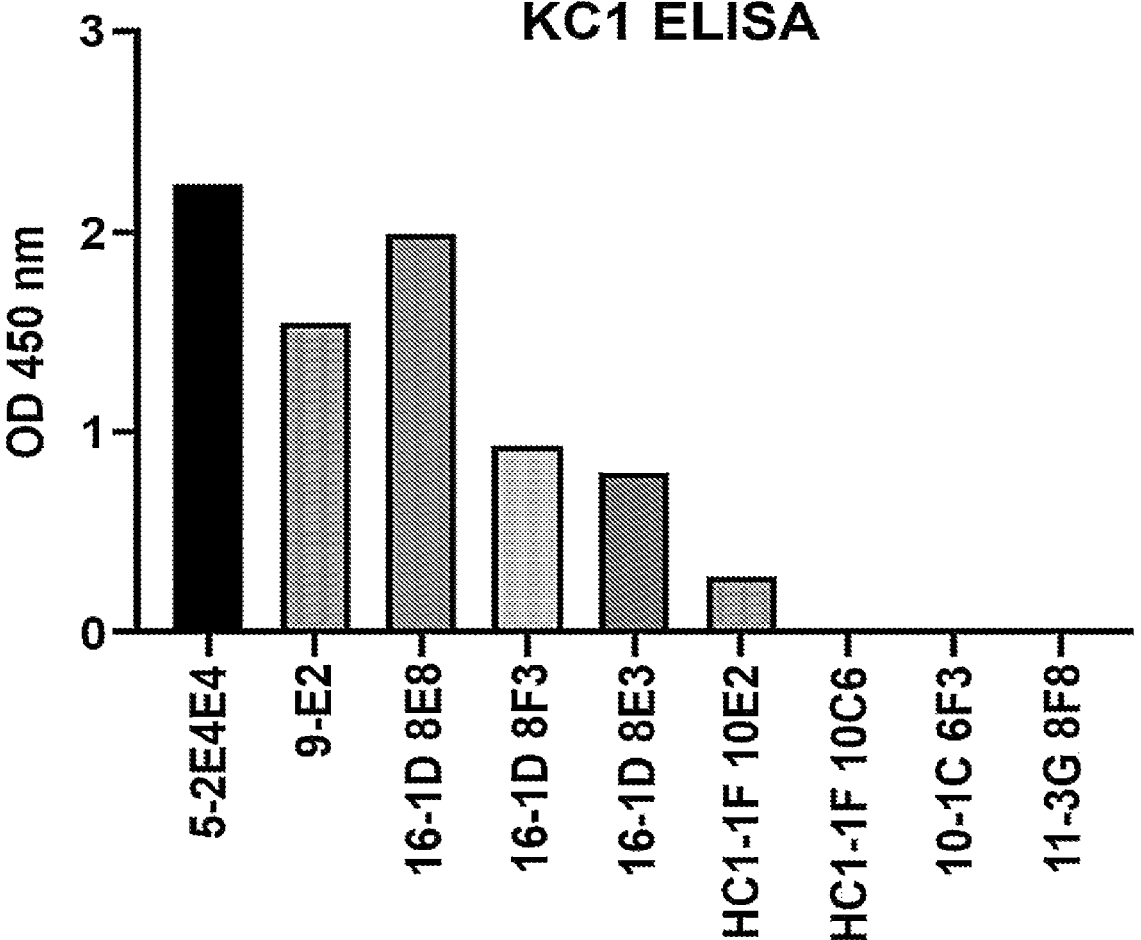
Figure 5D:
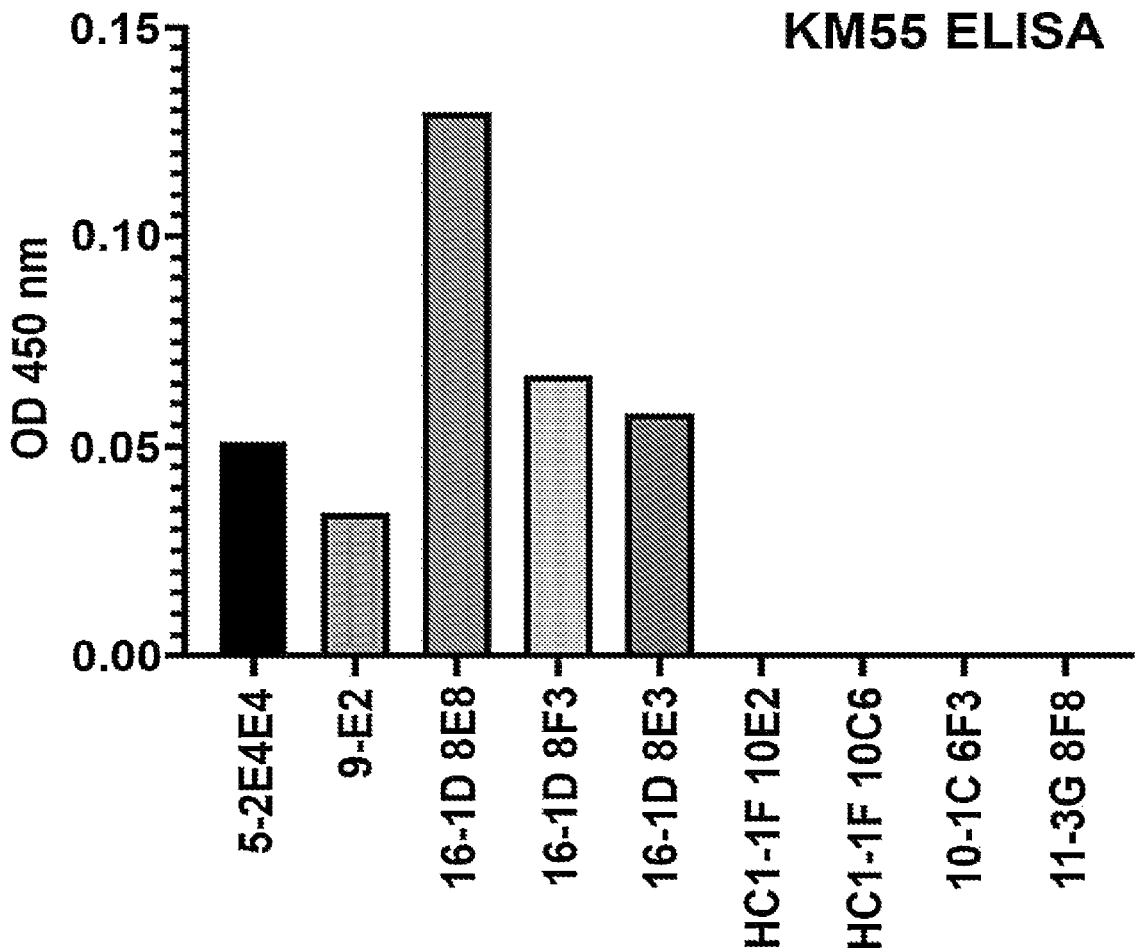

The galactose-deficient IgA1 cell line confirmed as a monoclonal human galactose-deficient IgA1 cell line was purified by using Jacalin-Sepharose Beads column and the anti-human galactose-deficient IgA1 IgG autoantibody cell line was purified by using protein G, after the purification, quantified and subjected them to ELISA binding analysis. The results show that IgG autoantibody at 16-3D5E3 (SEQ ID NO: 3) and 18-2E9D2 (SEQ ID NO: 6) can be binding with 5-2E4E4, 9-E2, 16-1D8E8, 16-1D8F3, 16-1D8E3 as the monoclonal galactose-deficient IgA1 (FIG. 5A, FIG. 5B), among which 5-2E4E4, 9-E2, 16-1D8E8, 16-1D8F3, 16-1D8E3 confirmed the galactose-deficient IgA1 by KCl ELISA and KM55 ELISA (FIG. 5C, 5D), which is beneficial to the subsequent analysis of immune complexes.

The embodiments encompassed herein are now described with reference to the following examples. These examples are provided for the purpose of illustration only, and the disclosure encompassed herein should in no way be construed as being limited to these examples, but rather should be construed to encompass any and all variations which become evident as a result of the teachings provided herein.

What is claimed is:

1. A reagent set for detecting the mechanism of IgA nephropathy and establishing a treatment strategy, which comprises a first IgG monoclonal antibody and a second IgG monoclonal antibody, wherein the first IgG monoclonal antibody comprises:
an HCDR1 comprising the amino acid sequence SEQ ID NO: 1;
an HCDR2 comprising the amino acid sequence SEQ ID NO: 2;
an HCDR3 comprising the amino acid sequence SEQ ID NO: 3;
an LCDR1 comprising the amino acid sequence SEQ ID NO: 7;
an LCDR2 comprising the amino acid sequence SEQ ID NO: 8; and
an LCDR3 comprising the amino acid sequence SEQ ID NO: 9;
wherein the second IgG monoclonal antibody comprises:
an HCDR1 comprising the amino acid sequence SEQ ID NO: 4;
an HCDR2 comprising the amino acid sequence SEQ ID NO: 5;
an HCDR3 comprising the amino acid sequence SEQ ID NO: 6;
an LCDR1 comprising the amino acid sequence SEQ ID NO: 10;
an LCDR2 comprising the amino acid sequence SEQ ID NO: 11; and
an LCDR3 comprising the amino acid sequence SEQ ID NO: 12.

2. A method for detecting galactose-deficient O-glycosyl IgA1, comprising:
(a) obtaining a biological sample from a subject; and
(b) using a first IgG monoclonal antibody and a second IgG monoclonal antibody in an immunoassay to detect galactose deficient O-glycosyl IgA1 in the subject;
wherein the first IgG monoclonal antibody comprises:
an HCDR1 comprising the amino acid sequence SEQ ID NO: 1;
an HCDR2 comprising the amino acid sequence SEQ ID NO: 2;
an HCDR3 comprising the amino acid sequence SEQ ID NO: 3;
an LCDR1 comprising the amino acid sequence SEQ ID NO: 7;
an LCDR2 comprising the amino acid sequence SEQ ID NO: 8; and an LCDR3 comprising the amino acid sequence SEQ ID NO: 9;
wherein the second IgG monoclonal antibody comprises:
an HCDR1 comprising the amino acid sequence SEQ ID NO: 4;
an HCDR2 comprising the amino acid sequence SEQ ID NO: 5;
an HCDR3 comprising the amino acid sequence SEQ ID NO: 6;
an LCDR1 comprising the amino acid sequence SEQ ID NO: 10;
an LCDR2 comprising the amino acid sequence SEQ ID NO: 11; and
an LCDR3 comprising the amino acid sequence SEQ ID NO: 12.

3. A method according to claim 2, wherein the subject is selected from the group consisting of IgA nephropathy (IgAN) subjects, lupus nephritis (LN) subjects and healthy subjects.

4. A method according to claim 2, wherein the biological sample is plasma, serum or blood.

5. A method for diagnosing a subject with IgA nephropathy (IgAN), comprising:
(a) using a first IgG monoclonal antibody or a second IgG monoclonal antibody, in an immunoassay; and
(b) determining whether the first IgG monoclonal antibody or the second IgG monoclonal antibody binds to galactose-deficient O-glycosyl polypeptide, the binding of the first IgG monoclonal antibody or the second IgG monoclonal antibody to galactose-deficient O-glycosyl polypeptide indicating that the subject has or is at risk of developing IgA nephropathy;
wherein the first IgG monoclonal antibody comprises:
an HCDR1 comprising the amino acid sequence SEQ ID NO: 1;
an HCDR2 comprising the amino acid sequence SEQ ID NO: 2;
an HCDR3 comprising the amino acid sequence SEQ ID NO: 3;
an LCDR1 comprising the amino acid sequence SEQ ID NO: 7;
an LCDR2 comprising the amino acid sequence SEQ ID NO: 8; and
an LCDR3 comprising the amino acid sequence SEQ ID NO: 9;
wherein the second IgG monoclonal antibody comprises:
an HCDR1 comprising the amino acid sequence SEQ ID NO: 4;

an HCDR2 comprising the amino acid sequence SEQ ID
NO: 5;

an HCDR3 comprising the amino acid sequence SEQ ID
NO: 6;

an LCDR1 comprising the amino acid sequence SEQ ID
NO: 10;

an LCDR2 comprising the amino acid sequence SEQ ID
NO: 11; and an LCDR3 comprising the amino acid sequence SEQ ID
NO: 12, wherein the galactose-deficient O-glycosyl
polypeptide for the binding of the first IgG monoclonal
antibody is selected from SEQ ID NO: 17 and SEQ ID
NO: 19, and wherein the galactose-deficient O-glycosyl
polypeptide for the binding of the second IgG mono-
clonal antibody is selected from SEQ ID NO: 13, SEQ
ID NO: 15, SEQ ID NO: 16 and SEQ ID NO: 19.

* * * * *